United States Patent [19]
Shimada et al.

[11] Patent Number: 5,267,985
[45] Date of Patent: Dec. 7, 1993

[54] DRUG DELIVERY BY MULTIPLE FREQUENCY PHONOPHORESIS

[75] Inventors: Jin Shimada, Falcon Heights; James E. Shapland, Shoreview, both, Minn.

[73] Assignee: Trancell, Inc., Roseville, Minn.

[21] Appl. No.: 16,796

[22] Filed: Feb. 11, 1993

[51] Int. Cl.⁵ .................. A61M 35/00; A61B 17/20
[52] U.S. Cl. .................... 604/290; 604/22; 128/24.1; 606/27
[58] Field of Search .............. 128/24.1, 200.16, 783, 128/804; 604/22, 310, 290; 606/27

[56] References Cited

U.S. PATENT DOCUMENTS

| | | | |
|---|---|---|---|
| 4,127,125 | 11/1978 | Takemoto et al. | 128/172.1 |
| 4,144,646 | 3/1979 | Takemoto et al. | 604/22 |
| 4,309,989 | 1/1982 | Fahim | 128/24 A |
| 4,372,296 | 2/1983 | Fahim | 128/24 A |
| 4,698,058 | 10/1987 | Greenfeld et al. | 604/266 |
| 4,767,402 | 8/1988 | Kost et al. | 604/22 |
| 4,948,587 | 8/1990 | Kost et al. | 424/435 |
| 4,953,565 | 9/1990 | Tachibaua et al. | 604/290 |
| 5,007,438 | 4/1991 | Tachibaua et al. | 604/290 |
| 5,151,085 | 9/1992 | Sakurai et al. | 604/22 |
| 5,161,521 | 11/1992 | kASAHARA ET AL. | 604/22 |
| 5,180,363 | 1/1993 | IDEMOTO ET AL. | 604/22 |
| 5,190,766 | 3/1993 | Ishihara | 604/22 |

FOREIGN PATENT DOCUMENTS

| | | |
|---|---|---|
| 445433 | 3/1973 | U.S.S.R. |
| 556805 | 1/1976 | U.S.S.R. |
| 591186 | 2/1978 | U.S.S.R. |
| 506421 | 3/1978 | U.S.S.R. |
| 910157 | 3/1982 | U.S.S.R. |

OTHER PUBLICATIONS

T. J. Antich, "Phonoresis: The Principles of the Ultrasonic Driving Force and Efficacy in Treatment of Common Orthopaedic Diagnosis", *The Journal of Orthopaedic and Sports Physical Therapy*, vol. 4, No. 2, pp. 99–102.

Donald M. Skauen et al., "Phonophoresis," *International Journal of Pharmaceutics*, 20 (1984) 235–245.

Primary Examiner—John G. Weiss
Attorney, Agent, or Firm—Merchant, Gould, Smith, Edell, Welter & Schmidt

[57] ABSTRACT

The present invention provides a method and apparatus for enhancing the diffusion of a substance to a local area of material or tissue by providing ultrasonic energy to the substance and material in two or more distinct frequencies simultaneously. Each of the distinct frequencies of ultrasonic energy is chosen to enhance permeation of the substance through one or more diffusion rate-limiting sections of the material.

13 Claims, 3 Drawing Sheets

FIG. 5B
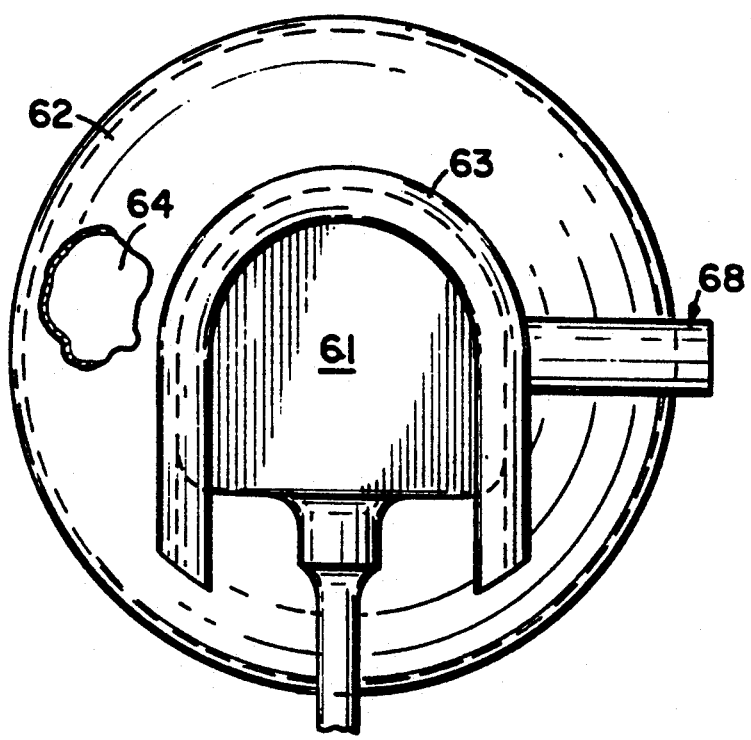
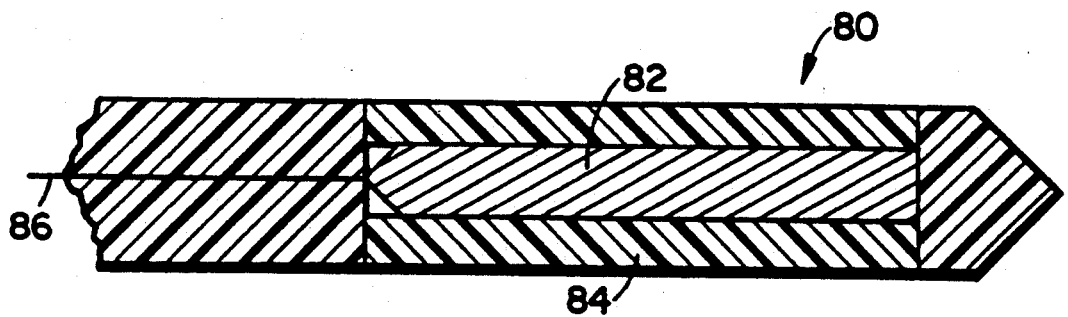
FIG. 6

DRUG DELIVERY BY MULTIPLE FREQUENCY PHONOPHORESIS

FIELD OF THE INVENTION

The present invention relates to a method and apparatus for enhancing the diffusion of drugs or other substances through materials using phonophoresis. More particularly, the present invention relates to enhancing the rate and depth of diffusion of drugs or other substances into targeted material using phonophoresis employing two or more distinct frequencies applied simultaneously.

DESCRIPTION OF RELATED ART

Phonophoresis has been recognized as a useful aid for enhancing the diffusion of drugs or other substances to tissue or other materials. One particularly beneficial use of phonophoresis involves the administration of drugs or other substances to living tissue which can provide intracellular localization of drugs or other substances such as anti-inflammatory agents.

For the purposes of the present invention, the term "substances" as used below will refer to drugs as defined by the medical community, as well as other substances which are desired to be delivered to tissue or other materials, with the delivery being enhanced through the use of phonophoresis. Examples of substances may include fixatives, physiological solutions, peptides, proteins, and numerous pharmacological agents.

As compared to the forms of systemic administration, the localized delivery of substances can provide important advantages over systemic administration (e.g., oral delivery or the injection of a substance), particularly when it is desired to provide a substance to a localized area of tissue. Localized delivery of substances to living tissue using diffusion is, however, limited when the tissue requiring treatment is located particularly far from the available delivery site or when the tissue to be treated is not homogeneous and presents different diffusion characteristics to the phonophoresis enhanced delivery of the substance.

As one example, the rate of transdermal substance delivery is typically limited by the rate of diffusion through the uppermost layer of skin, i.e., the stratum corneum which presents different absorption characteristics than the underlying tissue. During transdermal substance delivery where the ultimate goal is to diffuse the substance to and through tissue beneath a patient's skin, the drug molecules are first absorbed into the stratum corneum. Once absorbed, the drug molecules must diffuse through the stratum corneum to reach the underlying targeted tissue.

The relatively low permeability of the stratum corneum layer severely limits the number of therapeutic substances which can be transdermally delivered to a localized area of tissue below the stratum corneum at levels required for adequate treatment. Furthermore, ultrasonic energy at a frequency chosen to maximize diffusion across the stratum corneum may not provide sufficient penetration to significantly enhance diffusion to the targeted underlying tissue.

In addition to phonophoresis, iontophoresis can also be used to enhance the delivery of substances to materials, such as living tissue (either internally through a catheter or transdermally). Phonophoresis, however, offers several advantages over iontophoresis in such applications.

Iontophoresis requires ionization of the substances to enhance delivery while phonophoresis does not. As a result, diffusion of a number of substances is not significantly enhanced using iontophoresis.

The ultrasonic waves produced during phonophoresis also typically penetrate much deeper into the material than does the effective voltage difference in iontophoresis, thus providing for deeper penetration of the substances into the localized area. In, for example, living tissue, ultrasonic waves can penetrate up to five centimeters while iontophoresis typically transports substances through a depth of approximately one centimeter. Penetration of one centimeter is simply not sufficient when the goal of treatment is an area of tissue which may lie beyond one centimeter from the delivery site.

Another advantage of phonophoresis over iontophoresis in delivering substances to living tissue is the amount of time needed to diffuse a given amount of a substance. Typical transdermal treatment times using phonophoresis last approximately 10 minutes while transdermal treatments enhanced using iontophoresis typically last 20 to 30 minutes. As a result, the substances can reach their ultimate dosage levels in the treated tissue faster using phonophoresis to enhance delivery.

Tyle and Agrawala, "Drug Delivery by Phonophoresis", Pharmaceutical Research, Volume 6, No. 5 (1989), discusses the use of phonophoresis to enhance transdermal drug delivery. Tyle and Agrawala discuss the use of different frequencies to enhance absorption and note that, in general, tissue penetration is inversely proportional to frequency. As a result, lower frequencies provide deeper penetration of tissue while also providing a lower amount of energy per unit volume of tissue penetrated.

Although they note that frequency is inversely proportional to tissue penetration, Tyle and Agrawala disclose the use of ultrasound energy with only a single frequency to enhance transdermal drug delivery. Tyle and Agrawala also note that at least one study found that using different frequencies of ultrasound energy did not enhance transdermal delivery with any statistical significance.

U.S. Pat. No. 4,767,402 to Kost et al. discloses the use of ultrasound to enhance transdermal drug delivery to a patient's circulatory system—as opposed to enhancing the rate and penetration of diffusion of a substance to a localized area of tissue. To accomplish transdermal delivery of a drug or other substance into the patient's circulatory system, the Kost et al. reference discloses varying the frequency and intensity of the ultrasonic energy to affect the rate of transfer, thereby enhancing and/or controlling the rate of transfer of the substance to the circulatory system. The Kost et al. reference does not, however, disclose the use of more than one frequency of ultrasound energy at any given time to enhance transdermal delivery of a substance into a patient's circulatory system.

In addition, neither of the references described above discuss enhancing the rate and penetration of diffusion of substance delivered to internal tissue using phonophoresis, such as in catheter-based systems used to treat tumors and other internal tissues or body lumens.

Known methods of using phonophoresis to enhance diffusion of substances through materials or tissue have failed to adequately address situations involving non-homogeneous materials in which the first layer presents a barrier to diffusion, nor have they adequately addressed the problems associated with delivering the substance deep into a local area of tissue or material.

SUMMARY OF THE INVENTION

The present invention provides a method and apparatus for enhancing the diffusion of a substance to a local area of material or tissue by providing ultrasonic energy to the substance and material in two or more distinct frequencies simultaneously.

In the preferred methods involving non-homogeneous materials (e.g., transdermal applications or materials including an outer membrane), each frequency of ultrasonic energy is chosen to enhance permeation of the substance through one or more diffusion rate-limiting sections of the material. In transdermal delivery, for example, one frequency is preferably chosen to enhance permeation of the substance through the stratum corneum layer of the skin. Ultrasonic energy in one or more different frequencies is also simultaneously provided to enhance permeation of the substance through the tissue below the stratum corneum layer for subsequent diffusion deep into the local area of tissue to be treated.

Simultaneous use of two or more distinct frequencies of ultrasonic energy provides advantages not available to methods currently known for enhancing the diffusion of substances into a localized area of material or tissue.

By using specific frequencies, the rate and depth of diffusion into a material can be controlled to provide the most effective delivery system. Control and enhancement of the diffusion allows the delivery of a wider variety of substances to a local area of material through diffusion, some of which may not have been deliverable through diffusion using known techniques. In one particular method, the present invention results in a wider application of transdermal delivery of substances and a corresponding reduction in the disadvantages associated with oral or intravenous administration.

The methods of the present invention can also decrease the time required to administer substances using diffusion. That time savings can reduce the cost of administration, as well as the inconvenience to the patient when used for treatment of medical conditions.

Other advantages of using either multiple ultrasonic frequencies generated by a single transducer or using multiple transducers each driven by a single frequency include streaming, stirring, and a localized rise in temperature.

In streaming, the frequencies are chosen to create a high pressure gradient at the location of an interface, such as a skin surface or other semi-permeable membrane. The high pressure gradient enhances the net flow of the substance in the central region of the transducer energy field pattern in a phenomenon commonly referred to as streaming. The field pattern according to the preferred method of the present invention is designed to create continuous streaming phenomenon on both sides of a membrane or skin surface to enhance the transport of molecules across the tissue or membrane border.

Stirring, another advantageous phenomenon associated with the preferred methods according to the present invention, provides agitation in the area affected by the ultrasonic energy to prevent a low concentration layer from forming in contact with the membrane or tissue surface. The agitation and resulting prevention of low concentration areas helps to maintain a constant rate of diffusion in the preferred direction throughout the local area of material.

Another advantage of the method according to the present invention is the creation of a temperature rise of several degrees Celsius in the material surrounding the area treated. When treating living tissue in particular, that temperature rise is accompanied by a localized increase in blood perfusion which carries away substances diffused across the skin membrane or other rate-limiting section of tissue, thereby increasing the concentration gradient. That increase in the concentration gradient assists in the diffusion of more of the substance across the stratum corneum or other rate-limiting section of tissue. In transdermal delivery, limited hyperthermia may also enlarge skin pores, providing more diffusion surface and decreasing the amount of time required to diffuse a given amount of a substance through the patient's skin.

These and other advantages and features of the present invention will become apparent with reference to the drawings, the description of the preferred methods and the appended claims.

BRIEF DESCRIPTION OF THE DRAWINGS

FIG. 5B is a top view of the apparatus depicted in FIG. 5A.

FIG. 6 is a cross-sectional view of a catheter incorporating an ultrasonic transducer which can be used according to the preferred methods of the present invention.

DETAILED DESCRIPTION OF THE PREFERRED AND ALTERNATE METHODS OF THE PRESENT INVENTION

As described above, the present invention involves the use of phonophoresis to enhance the diffusion of a substance through a material. Although specific medical applications for the method according to the present invention will be described below, they should not be construed as limiting the invention to methods involving the delivery of drugs or other substances to living tissue. In particular, the methods according to the present invention may also be used in industrial processing or any other application involving materials in which substances must be diffused. Examples of such applications could include: enhanced pigment penetration in printing processes, general processes for molecular separation and numerous other applications.

As described above, the method of using phonophoresis to enhance diffusion through materials is particularly useful when those materials are non-homogeneous in nature. One particular class of applications which present non-homogeneous materials through which substances must be diffused include transdermal drug delivery, as well as delivery through any diffusion limiting membranes covering an underlying material.

In those applications, the membrane typically presents a rate limiting barrier which slows diffusion of a substance to the material underneath the membrane. In transdermal applications, the rate limiting membrane is typically the stratum corneum layer of a patient's skin. FIGS. 1-5, discussed below, describe one preferred method according to the present invention wherein a membrane 24, such as skin or other rate-limiting layer, presents a barrier to diffusion of a substance to the tissue underlying that membrane.

Figure 1:
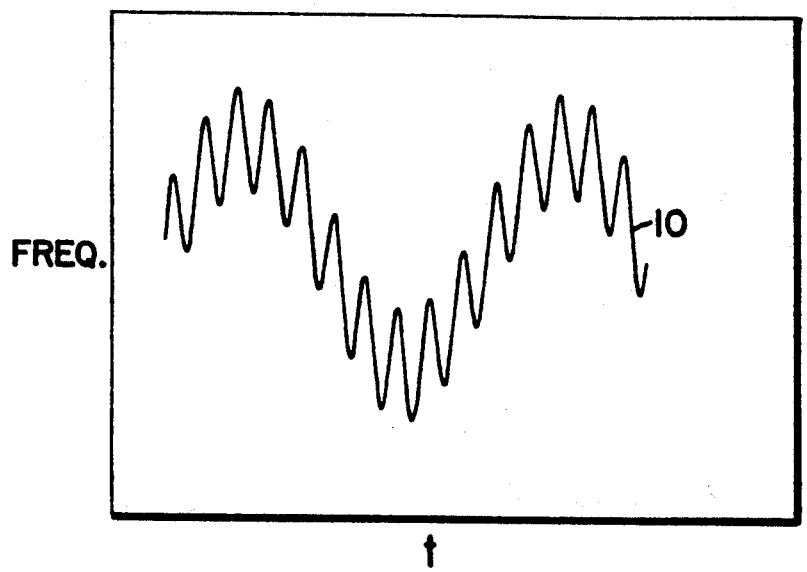
FIG. 1 is a graph of a dual frequency energy wave associated with the present invention.

Referring to FIG. 1, which depicts a graph of a preferred ultrasonic wave 10 produced by using the preferred method of the present invention. An acoustic energy wave 10 having the characteristics shown in FIG. 1 can be produced either by: 1) driving a single transducer with voltage corresponding to the sum of the voltages required to produce each frequency desired; or 2) or by driving a number of transducers, each with a voltage corresponding to a single output frequency of the transducer as desired. Examples of each of these configurations are shown in FIGS. 2 and 3.

Figure 2:
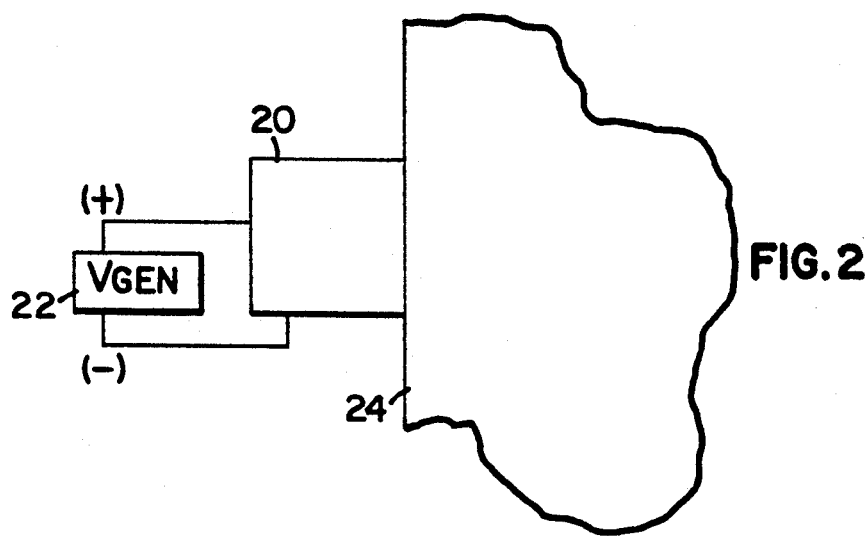
FIG. 2 is a schematic diagram of a single transducer driven by multiple frequencies to produce the preferred dual frequency ultrasound waves of the present invention.

As shown in FIG. 2, the transducer 20 is driven by a voltage source 22 and is located proximate a membrane 24 covering a tissue area 26. The voltage used to produce the multiple frequencies according to the present invention can be characterized by the following equation: $V_{gen} = A_1 \cos w_1 t + A_2 \cos w_2 t$, where $V_{gen}$ is the resulting voltage provided to the transducer 20, $A_x$ is the amplitude of each desired signal and $w_x$ is the desired frequency of each signal.

The preferred frequency range for each signal is from 100 Hz to 100 MHz. Preferred combinations for two-frequency methods include 1 MHz & 3 MHz; 3 MHz & 9 MHz, and 5 MHz & 15 MHz. It will, however, be understood that any combination of two or more frequencies is contemplated for use in the method according to the present invention.

Figure 3:
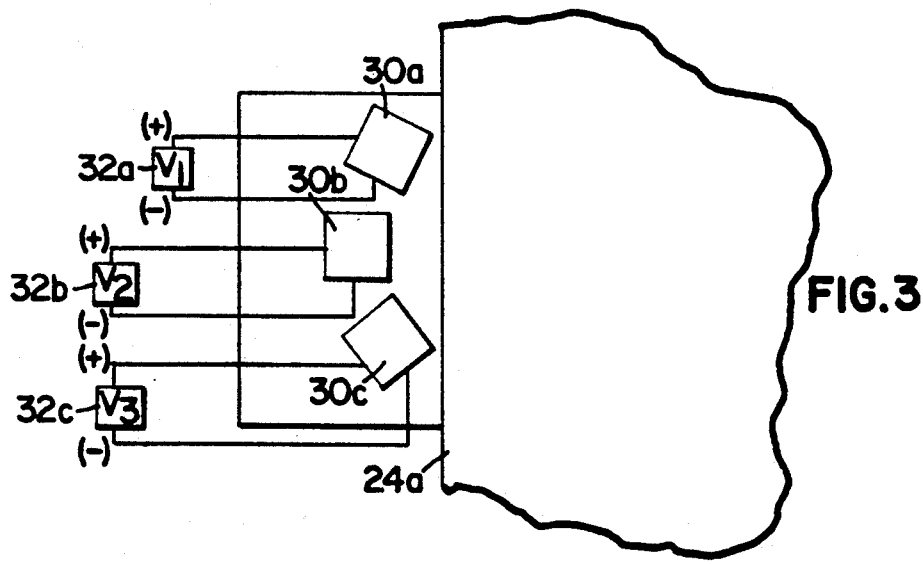
FIG. 3 is a schematic diagram illustrating the use of multiple transducers each producing a single frequency of ultrasonic energy directed at the same location on the skin of a patient.

Alternately, as depicted in FIG. 3, a number of transducers 30a, 30b and 30c (referred to generally as 30) can be driven by separate voltage sources 32a, 32b, and 32c (referred to generally as 32) which are adjusted to produce a desired frequency from each transducer 30. Each transducer 30 produces a single frequency ultrasonic wave, all of which are substantially directed at a particular point on the membrane 24a which covers an area of tissue 26a. That apparatus generally provides the same effect as the system described in FIG. 2.

Figure 4:
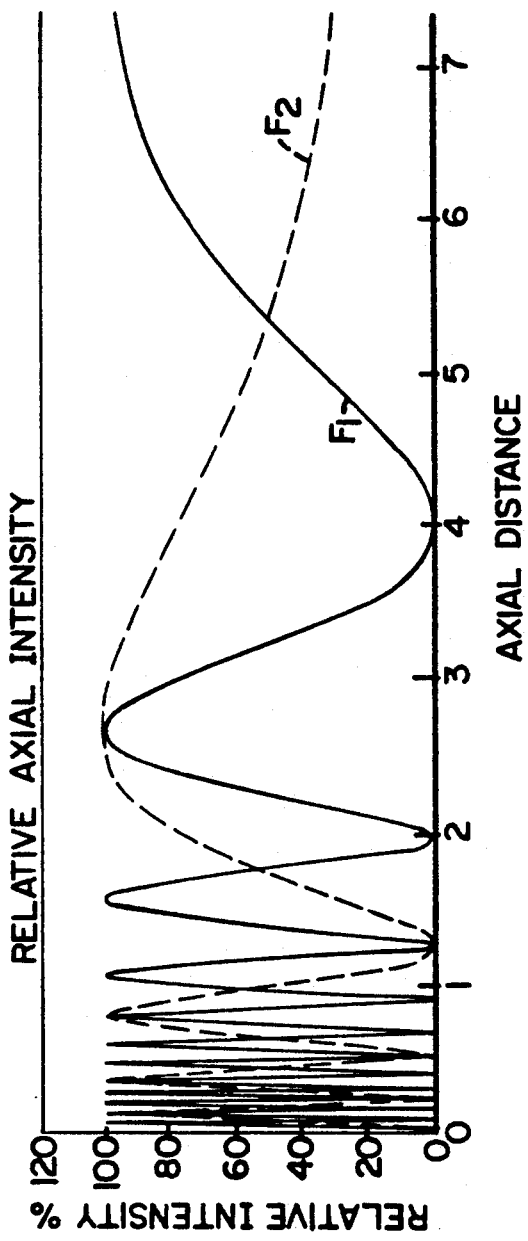
FIG. 4 is a graph of the relative axial intensity of the ultrasonic energy produced by a dual frequency ultrasound system as a function of axial distance.

Referring now to FIG. 4, the relative axial intensity of a preferred dual frequency ultrasound system is depicted in the graph of FIG. 4. The relative intensity of two distinct frequencies, $F_1$ at 1 MHz and $F_2$ at 3 MHz, shows that at increasing distances from the transducer or transducers each particular frequency component has a different axial intensity which varies over the distance.

The intensities typically do not coincide and, as a result, the use of a multiple frequency system can provide a more uniform axial intensity over a greater distance than can a single frequency ultrasound system. For example, at the distance of 4 units from the transducer, the intensity of $F_2$ is at 0% while the intensity of $F_1$ remains at approximately 75%. This particular graph shows the advantage of a dual frequency system in that deeper penetration may be possible due to the differences in axial intensity as a function of axial distance.

Figure 5A:
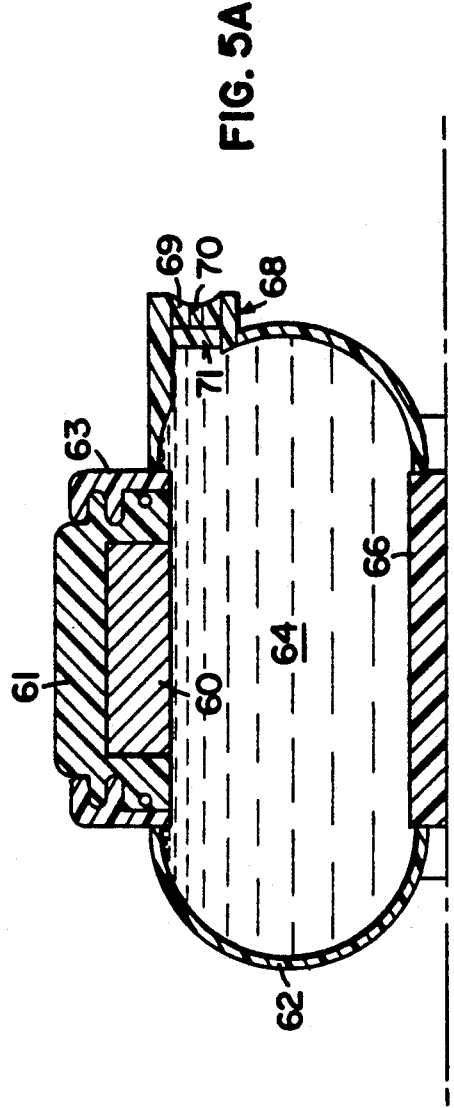
FIG. 5A is a cross-sectional view of one preferred embodiment of an apparatus incorporating a transducer, pouch and semi-permeable membrane for transdermal drug delivery.

FIGS. 5A and 5B depict one preferred embodiment of an apparatus used to enhance transdermal delivery according to the present invention. The transducer 60 is preferably mounted in a slide-type housing 63 attached to pouch 62. The transducer 60 is preferably backed by an insulating, acoustically reflective material 61 which focuses the ultrasonic energy downward, toward the area to be treated.

The use of a pouch 62, which is preferably flexible and deformable, allows the drug solution 64 in the pouch 62 to conform to and uniformly contact a variety of irregularly shaped surfaces. In the preferred embodiment, the bottom wall 66 on the pouch 62 is constructed of a microporous, permeable or semi-permeable membrane material such as microporous polycarbonate, polytetrafluoroethylene, nylon or polyacrylonitrile. Those substances are provided only as examples of possible materials and should not be considered as limiting the scope of the present invention.

The preferred pouch material is flexible and will function to contain fluid within the pouch until subjected to ultrasonic energy from the transducer 60 to drive the substance contained in the pouch 62 through a patient's skin and to the localized area of tissue.

The preferred transducer 60 is preferably in the shape of a plate and covers a majority of the upper surface of the pouch 62. The transducer 60 is preferably applied to the pouch 62 using an adhesive or mechanical process to ensure adequate contact between the transducer 60 and the pouch 62 to efficiently transfer ultrasonic energy from the transducer 60 to the fluid 64 in the pouch 62 and, subsequently, into the local area of tissue needing treatment.

In the preferred embodiment, the pouch 62 is constructed with a uniform contact area 66 between the pouch 62 and a skin surface area against which the pouch 62 is placed. That uniform contact area 66 preferably remains constant, regardless of the shape of the skin surface to be treated. In addition, pressure sensitive adhesives may be applied to the bottom of the pouch 62 to ensure adequate contact with the skin surface. The adhesive promotes efficient transfer of the ultrasonic energy from the transducer 60 to the skin surface through fluid 64.

The drug to be delivered transdermally can be contained in the fluid 64 in the pouch 62 or, alternately, the pouch 62 can additionally include an injection channel 68 through which substances could be introduced into the pouch 62 for transfer to the patient. As an example, the channel 68 depicted in FIG. 6 includes a tubular member 69 which defines an orifice 70 for receiving a cannula. A self-sealing plug 71 is disposed at the end of the orifice 70 to block access to the interior of the pouch 62. Fluid is then introduced into the pouch 62 by inserting a cannula into the orifice 70 and forcing the tip of the cannula through the orifice 70 and into the pouch 62.

As an alternative to providing the drug or other substance in solution form, it can be provided in the form of gel or a polymer matrix material containing the drug or other substance. That gel or polymer matrix material is then placed between a transducer and the area to be treated. Such forms are known in the art and will not be described herein.

In use, the transducer 60 and pouch 62 are placed on the surface of a patient's skin located above the local area of tissue to be treated. The medication to be delivered is provided in the forms described above, i.e., in solution in the pouch 62 or in any other appropriate form. Once in place, the transducer 60 is driven with a voltage needed to produce ultrasonic waves of two distinct frequencies simultaneously. In one preferred transdermal enhancement method, one frequency is 1 MHz and the second frequency is 3 MHz. That particular combination of frequencies provides optimum diffusion of the drug across the stratum corneum while also maximizing penetration of a drug or other substance into the local area of target tissue.

As discussed above, other contemplated frequency combinations include 3 MHz+9 MHz as well as 5 MHz+15 MHz.

In one specific example, the tissue to be treated is a bone joint using an anti-inflammatory agent such as dexamethasone. The dexamethasone is provided in pouch 62. The frequencies chosen for delivery are 3 MHz and 1 MHz with amplitudes of 100 volts, peak to peak, and 35 volts, peak to peak, respectively. Treatment times for this method vary between individual patients, but generally are in the range of 15-30 minutes to reach a penetration of 1-2 cm.

The method and apparatus described above are particularly useful when the material through which a substance must be diffused presents an outer surface with or without a diffusion limiting membrane. The present invention is also useful for enhancing the diffusion of a substance to a localized internal area of a material. One particular example of such a situation is the delivery of a substance to a tumor or other object in the body of a patient through the use of a catheter-based delivery system.

One version of a catheter designed to deliver a drug or other substance to internal tissue using phonophoresis is depicted in FIG. 6. As shown there, the catheter 80 includes a transducer 82 disposed within a drug delivery chamber and is activated by electrical energy traveling along wires down a lumen 86 of the catheter 80. In one preferred embodiment, the drug or other substance can be held in a gel or polymer matrix material 84 formed around the transducer 82. Such a catheter is more fully described in co-pending U.S. patent application Ser. No. 07/973,263, filed on Nov. 9, 1992, titled POLYMER MATRIX DRUG DELIVERY APPARATUS AND METHOD, which is hereby incorporated by reference.

Alternatively, the substance can be pumped to the chamber using additional lumens, the construction of which will be known to those skilled in the art.

In use, the catheter 80 is advanced through the body of a patient until it is located in or near the tissue requiring treatment. Once in place, the transducer 82 is activated to produce multiple frequencies of ultrasonic energy simultaneously, as described above. Once activated, the drug is driven from the catheter 80 and into the tissue requiring treatment. Multiple frequency phonophoresis is especially useful in conjunction with catheter-based delivery when the tissue to be treated is non-homogeneous in nature, surrounded by a membrane or other barrier which limits the rate of diffusion to the targeted local area of tissue, and/or when the tissue to be treated is located at relatively large distances from the delivery site.

Although specific methods and apparatus have been described above, it will be understood the invention is to be limited only by the claims and the equivalents thereof.

We claim:

1. A method of enhancing diffusion of a substance through material comprising the steps of:
   a) providing said substance proximate said material;
   b) providing a first component of ultrasonic energy to said substance, said first component of ultrasonic energy having a first frequency;
   c) providing a second component of ultrasonic energy to said substance simultaneous with said first component of ultrasonic energy, said second component of ultrasonic energy having a second frequency, said second frequency differing from said first frequency, whereby diffusion of said substance through said material is enhanced.

2. The method of claim 1, further comprising the step of selecting said first frequency to enhance diffusion of said substance through a first portion of said material.

3. The method of claim 2, wherein said first portion of said material is a diffusion rate limiting membrane.

4. The method of claim 2, wherein said material is living tissue and further wherein said first portion of said material is a stratum corneum layer of skin.

5. The method of claim 4, wherein said first frequency lies in the range of 10 kHz to 100 MHz.

6. The method of claim 1, further comprising the step of selecting said second frequency to enhance diffusion of said substance through a second portion of said material.

7. The method of claim 6, wherein said material is living tissue below a layer of skin.

8. The method of claim 7, wherein said second frequency lies in the range of 100 Hz−20 MHz.

9. The method of claim 1, wherein said first and second components of ultrasonic energy are provided by a single transducer.

10. The method of claim 1, wherein said first and second components of ultrasonic energy are provided, respectively, by first and second transducers.

11. A method of enhancing diffusion of a substance through material comprising the steps of:
   a) providing said substance proximate said material;
   b) providing a first component of ultrasonic energy to said substance, said first component of ultrasonic energy having a first frequency;
   c) selecting said first frequency to enhance diffusion of said substance through a first portion of said material;
   d) providing a second component of ultrasonic energy to said substance simultaneous with said first component of ultrasonic energy, said second component of ultrasonic energy having a second frequency;
   e) selecting said second frequency to enhance diffusion of said substance through a second portion of said material, whereby diffusion of said substance throughout said first and second portions of said material is enhanced.

12. The method of claim 11, wherein said first and second components of ultrasonic energy are provided by a single transducer.

13. The method of claim 11, wherein said first and second components of ultrasonic energy are provided, respectively, by first and second transducers.

* * * * *